United States Patent [19]
Holmes

[11] Patent Number: 5,511,432
[45] Date of Patent: Apr. 30, 1996

[54] HOLDER FOR CORRUGATED PAPERBOARD TEST SPECIMEN DURING EDGE COMPRESSION TEST

[76] Inventor: William C. Holmes, 170 Anderson St., Portland, Me. 04101

[21] Appl. No.: 419,082

[22] Filed: Apr. 10, 1995

[51] Int. Cl.⁶ .................................................. G01N 3/02
[52] U.S. Cl. ................................................ 73/856; 73/860
[58] Field of Search ....................... 73/849, 853, 856, 73/860, 847

[56] References Cited

U.S. PATENT DOCUMENTS

| | | | |
|---|---|---|---|
| 3,224,259 | 12/1965 | Nicola | 73/860 |
| 4,535,636 | 8/1985 | Blackburn et al. | 73/856 |
| 4,958,522 | 9/1990 | McKinlay | 73/847 |
| 5,297,441 | 3/1994 | Smith et al. | 73/860 |
| 5,305,634 | 4/1994 | Suga et al. | 73/856 |

*Primary Examiner*—Richard Chilcot
*Assistant Examiner*—Max Noori
*Attorney, Agent, or Firm*—Frederick R. Cantor

[57] ABSTRACT

A holder for a corrugated paperboard test specimen is designed to orient the specimen in a vertical plane so that the specimen can be subjected to an edgewise compression test. The holder includes upper and lower clamps that grip the upper and lower surfaces of the specimen, leaving an intermediate section of the specimen unsupported; the specimen will experience a buckling action in the unsupported section as a response to progressively increased vertical loads. Each clamp includes a spring-biased clamping pad that can be retracted manually to permit insertion of a test specimen into the clamping space.

8 Claims, 2 Drawing Sheets

HOLDER FOR CORRUGATED PAPERBOARD TEST SPECIMEN DURING EDGE COMPRESSION TEST

BACKGROUND OF THE PRESENT INVENTION

SUMMARY OF THE PRESENT INVENTION

This invention relates to a device for holding a corrugated paperboard test specimen during an edge compression test on the specimen.

An edge compression test on a corrugated paperboard specimen is performed to test the compressive strength of the specimen in planes parallel to the major surfaces of the specimen. Commonly the test specimen is a square section cut from a representative corrugated paperboard panel used in the manufacture of paperboard (fibreboard) shipping cartons. The square test section typically measures two inches on a side (which provides a specimen face area of four square inches).

The edge compression test is performed by standing the test specimen upright (on edge) within a testing machine so that an upper edge of the specimen is presented to an upper platen in the machine, and a lower edge of the specimen is presented to a lower platen in the machine. The lower platen is powered upwardly toward the upper platen at a controlled rate so that compressive forces are applied to the specimen along vertical planes paralleling the major surfaces of the upright test specimen.

The test specimen is usually arranged so that the flutes of the reinforcement corrugations in the specimen are oriented vertically, i.e., parallel to the directions of the applied compressive forces. This is done so that the corrugated paperboard will be tested in the direction of maximum strength, i.e., parallel to the flutes.

In order to hold the test specimen in a precise vertical upright position in the test machine during the edge compression test, it is the usual practice to mount the specimen in a holder while the test is being performed. The holder keeps the specimen precisely vertical during the test so that the applied forces are applied to the specimen in the proper (desired) direction. This ensures repeatability of the testing process, whereby test results with different samples can be compared with the necessary quality assurance and confidence.

The present invention relates to a holder for a corrugated paperboard test specimen while the specimen is being tested for edgewise compressive strength. The preferred holder construction comprises a lower clamp means for holding a lower end portion of the specimen, an upper clamp means for holding an upper portion of the system, and an upright slide mechanism for slidably supporting the upper clamp means, whereby the application of a vertical compressive force to the upper and lower clamp means subjects the specimen to a potentially destructive vertical test force.

The upper and lower clamp means are designed so that the clamped areas of the specimen are subjected to clamp forces that are sufficient for the desired clamp action, while at the same time not producing any undesired deformation of the specimen surface. Such deformation is undesirable in that the specimen is thereby weakened so as to adversely affect the test result or its meaning.

A sufficient clamp force is necessary to avoid slippage between the clamp mechanism and the specimen. Such slippage would adversely affect the test result in that vertical strain produced by the load forces would appear as a squashing or indentation of the specimen end edges, rather than deflection of the unclamping areas of the specimen. The machine readings would then not be representative of the edgewise compressive strength of the specimen.

The preferred specimen holder embodying the invention utilizes clamp mechanisms wherein clamp pads are biased by coil springs that produce a consistent uniform clamp force, sufficient to prevent slippage of the specimen without deforming the specimen surface, in contact with the clamp mechanisms. The clamp surfaces are preferably treated or formed to achieve a relatively high coefficient of friction between the clamp surfaces and the test specimen surfaces; the aim is to prevent vertical slippage between the specimen and the clamp mechanisms, without employing excessively high clamp forces, as might deform the specimen surfaces.

The holder of the present invention is designed so that the clamp pads are easily retracted away from the associated vertical clamp walls, whereby test specimens can be quickly and easily inserted into the clamp mechanisms without undue effort or precision. Each clamp pad has a horizontal rod extending into a channel spaced from the associated vertical clamp wall; a manually rotatable nut is threaded onto each rod within the associated channel. By rotating each nut in a particular direction it is possible to retract the associated clamp pad. By rotating each nut in the opposite direction the associated rod is moved linearly to enable the respective clamp pad to advance against the test specimen; a coil spring surrounding each rod exerts a clamp force on the associated pad.

The holder is designed for easy manual opening and closing of the upper and lower clamp mechanisms. The clamp mechanisms are constructed so that the clamp force is essentially constant and independent of the thickness of the test specimen. Variations in the test specimen thickness do not affect the clamp force.

Further features and advantages of the test specimen holder will be apparent from the attached drawings and accompanying description of an illustrative embodiment of the invention.

In summary, and in accordance with the above discussion, the foregoing objectives are achieved in the following embodiments:

1. A holder for a corrugated paperboard test specimen that is to be tested for edgewise compression strength:

said holder comprising a support mechanism having a vertical slideway;

a lower specimen clamp means carried by said support mechanism; and an upper specimen clamp means slidably mounted on said slideway for vertical movement toward or away from said lower clamp means.

2. The holder, as described in paragraph 1, wherein each said clamp means comprises a vertical clamp surface adapted to engage one face of a test specimen, a horizontally movable pad adapted to engage the other face of the test specimen, and spring means biasing said pad toward the associated clamp surface.

3. The holder, as described in paragraph 2, wherein each said clamp means further comprises a manual means for moving the respective pad away from the associated clamp surface to permit insertion of a test specimen into the upper and lower clamp means.

4. The holder, as described in paragraph 2, wherein each said clamp means further comprises a manual means for moving the respective pad away from the associated clamp surface to permit insertion of a test specimen into the upper and lower clamp means; and each said manual means comprises a linear rod extending horizontally from the respective pad, and a rotary nut threaded onto each respective rod, whereby manual rotation of the rod moves the rod and associated pad.

5. The holder, as described in paragraph 4, wherein each said spring means comprises a coil spring encircling the respective linear rod.

6. The holder, as described in paragraph 1, wherein said support mechanism comprises a vertical block having a vertical recess;

said vertical slideway comprising a guide element located in said recess;

said upper clamp means having a slide element slidably mounted on said guide element for vertical movement; and said lower clamp means comprising a vertical wall secured to said vertical block, a horizontal wall extending from said vertical wall, and a movable pad slidably mounted on said horizontal wall for movement toward or away from said vertical wall.

7. The holder, as described in paragraph 6, wherein said upper clamp means comprises a second vertical wall affixed to said slide element, a second horizontal wall extending from said second vertical wall, and a second movable pad slidably mounted on said second horizontal wall for movement toward or away from said second vertical wall.

8. The holder, as described in paragraph 7, wherein said lower clamp means further comprises a first channel secured to said first horizontal wall, a first horizontal rod extending from said first pad through said channel, a first coil spring encircling said first rod in the space between said first pad and said channel, and a first rotary nut threaded onto said first rod within said first channel;

said nut being manually rotatable to move said first rod and the associated pad away from said first vertical wall; and said coil spring having one end thereof abutting said first pad to normally bias said first pad toward said first vertical wall in the absence of an opposing force by said first nut.

9. The holder, as described in paragraph 8, wherein said upper clamp means further comprises a second channel secured to said second horizontal wall, a second horizontal rod extending from said second pad through said second channel, a second coil spring encircling said second rod in the space between said second pad and said second channel, and a second rotary nut threaded onto said second rod within said second channel;

said second nut being manually rotatable to move said second rod and the associated pad away from said second vertical wall; and said second coil spring having one end thereof abutting said second pad to normally bias said second pad toward said second vertical wall in the absence of an opposing force generated by said second nut.

10. The holder, as described in paragraph 9, wherein said first and second vertical walls have vertical faces adapted to grip one face of a test specimen, and said first and second pads have vertical faces adapted to grip the other face of a test specimen; and said vertical faces having friction gripper properties to prevent the test specimen from slipping on said vertical faces.

11. The holder, as described in paragraph 1, wherein each said clamp means comprises a vertical clamp surface adapted to engage one face of a test specimen, a horizontally movable pad adapted to engage the other face of the test specimen, and spring means normally biasing said pad toward the associated vertical clamp surface; and said vertical clamp surfaces and said pads having frictional grip properties to prevent the test specimen from vertical slippage.

12. The holder, as described in paragraph 1, wherein each said upper and lower clamp means comprises a movable pad and a facing vertical wall that cooperatively form a side access slot; and each said clamp means being openable by a horizontal movement of the respective pad away from the associated vertical wall, whereby the side access slots are widened to permit insertion of a test specimen into the clamp means.

A BRIEF DESCRIPTION OF THE DRAWINGS

DESCRIPTION OF THE PREFERRED EMBODIMENT OF THE PRESENT INVENTION

Figure 1:
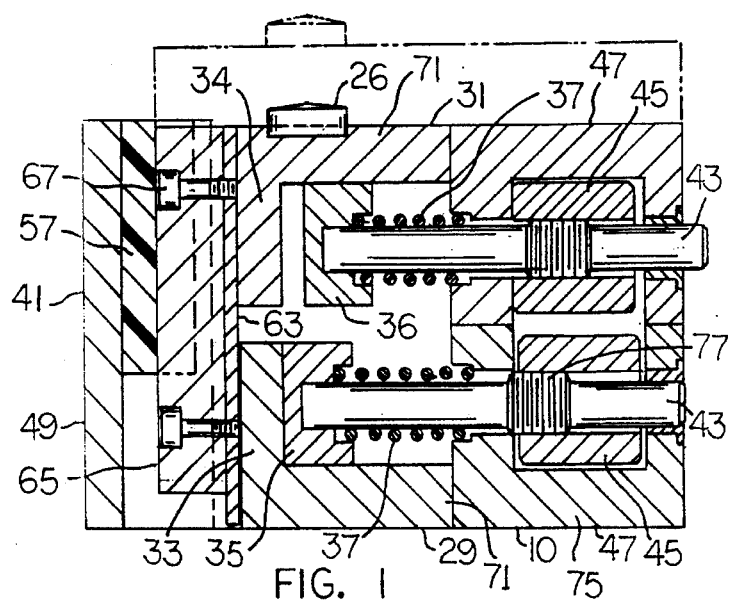
FIG. 1, is a sectional view, taken on line 1—1 in FIG. 2, and showing internal features of a test specimen holder that constitutes one embodiment of the invention.
Figure 2:
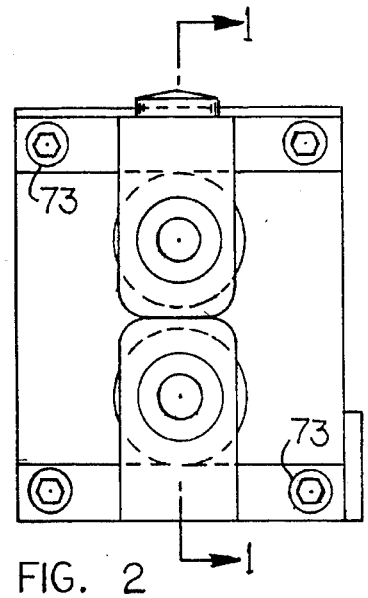
FIG. 2, is a right end elevational view, of the FIG. 1 specimen holder.

FIG. 1, is a sectional view, taken on line 1—1 in FIG. 2, and showing internal features of a test specimen holder that constitutes one embodiment of the invention.

Figure 6:
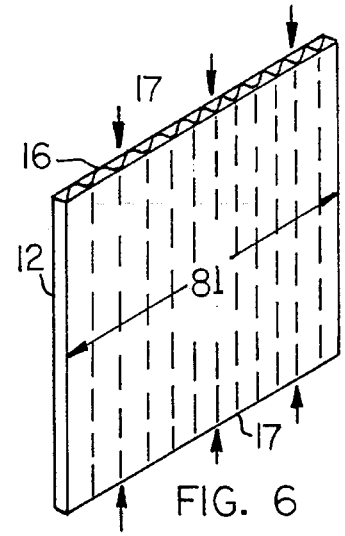
FIG. 6, is a perspective view, of a corrugated paperboard test specimen of the type that can be placed in the holder shown in FIGS. 1 through 5.

FIG. 6, is a perspective view, of a corrugated paperboard test specimen of the type that can be placed in the holder shown in FIGS. 1 through 5.

Figure 7:
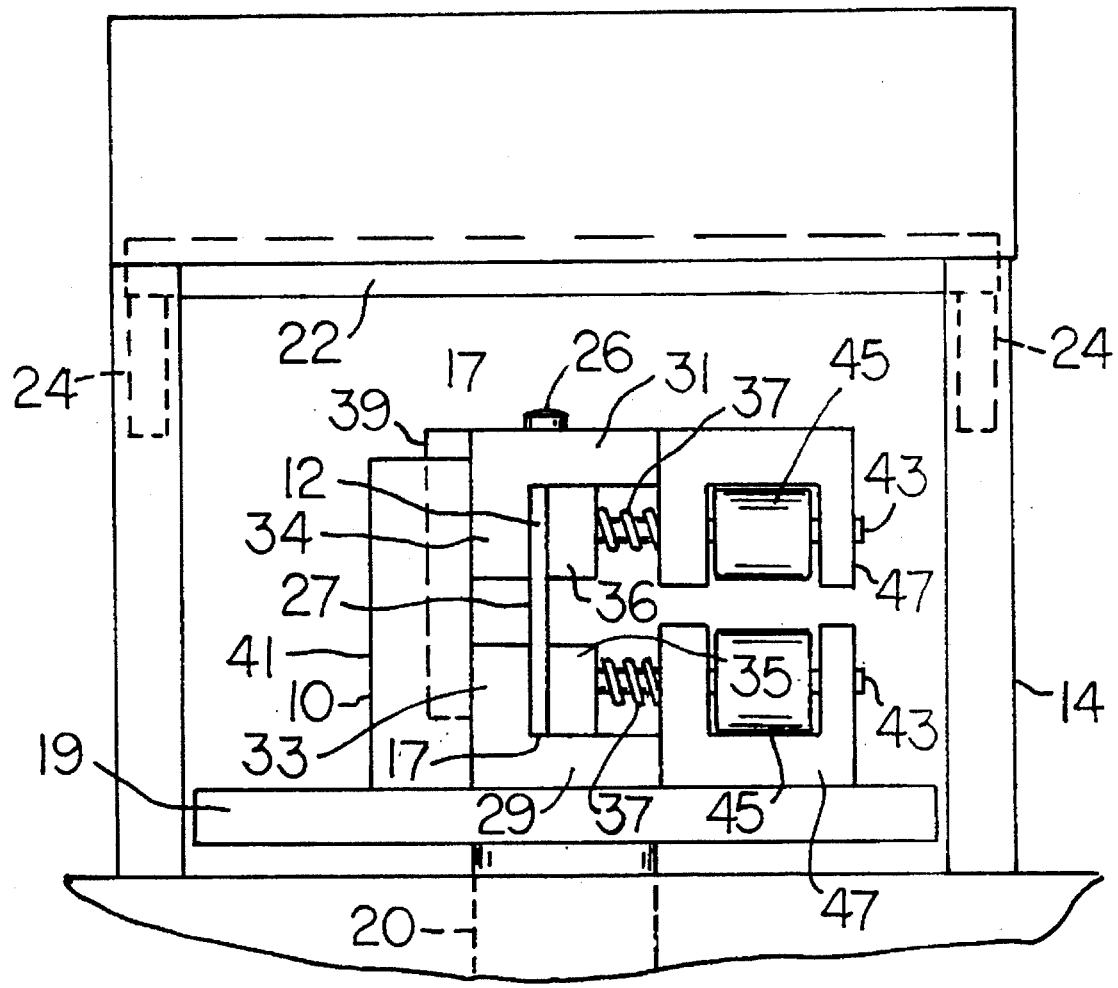
FIG. 7, is an elevational view, of the FIG. 1 specimen holder, taken on a reduced scale, and showing the holder placed in a testing machine.

FIG. 7, is an elevational view, of the FIG. 1 specimen holder, taken on a reduced scale, and showing the holder placed in a testing machine.

The drawings show a holder 10 for a test specimen 12. FIG. 6 shows the test specimen 12 separated from the holder, whereas FIG. 7 shows, on a reduced scale, the test specimen 12 inserted into the holder. The holder is shown in position in a testing machine 14 prior to an edge compression test.

Referring to FIG. 6, test specimen 12 comprises a flat panel defined by two face-forming paper (fibre) sheets and a corrugated liner sheet 16. The corrugations form flutes that run in the vertical direction. The crest surfaces of the corrugations are glued to the inner surfaces of the face-forming sheets to provide a reinforced panel.

An edge compression test is performed on the specimen 12 to provide information on the integrity of the adhesive connections between the corrugated liner sheet 16 and the face-forming sheets, as well as the overall compression strengths of the paper materials used.

The edge compression test is performed by orienting the test specimen 12 in an upright vertical condition, with the corrugation flutes extending vertically. Vertical loads are applied to the upper and lower edges 17 of the specimen, as denoted by the arrows in FIG. 6. The vertical loads are applied along the entire length of the specimen (dimension 81 in FIG. 6).

FIG. 7 shows the test specimen mounted within a holder 10 prior to the start of an edge compression test. The holder keeps the specimen in an upright vertical condition during the progress of the test, so that the test is repeatable and representative of the specimen's edge compressive strength.

Testing machine 14 comprises a lower platen 19 mounted on the upper end of a vertical support tube 20. An electric motor, not shown, has a screw connection with support tube 20, such that the platen 19 can be raised at a desired rate e.g., one-half inch per minute.

The testing machine includes an upper platen 22 that is connected at its corners to load cells 24. Each load cell 24 comprises one or more electrical strain gauges that are electrically connected to recording instrumentation in the testing machine, whereby the loading and deflection of platen 22 can be recorded.

As platen 19 is powered upwardly, a button 26 on the upper surface of holder 10, contacts platen 22. Further upward movement of platen 19 applies vertical loads to holder 10 and to test specimen 12, located within the holder 10. Eventually, the increased vertical loadings cause the specimen 12 to buckle in approximately a zone midway between the upper and lower edges of the specimen 12. In FIG. 7, the buckling zone of the specimen 12 is indicated by numeral 27. The peak loading at the point of buckling is indicative of the edgewise compressive strength of the specimen.

As shown generally in FIG. 7, holder 10 comprises a lower specimen clamp means 29, and an upper specimen clamp means 31. Each clamp means comprises a vertical wall 33 or 34 engaged with one face of the test specimen, and a movable pad 35 or 36, engaged with the other face of the test specimen. Each pad 35 or 36 is biased horizontally against the specimen by a coil spring 37, whereby the pad develops a controlled (known) clamping force on the test specimen. Typically the clamping force is ten pounds per square inch.

The pad clamping force on the test specimen is controlled, in order to prevent vertical slippage of the specimen, without unduly indenting or deforming the specimen surface. If the clamp force is too high the specimen can be unduly squeezed so as to compromise the strength of the specimen at the upper and lower limits of the clamped surfaces. If the clamp force is too low the specimen can experience vertical slippage relative to the clamp surfaces; such vertical slippage can unduly load and deform the upper and lower edges 17 of the specimen, such that the instrument readings no longer measure the buckling point in zone 27.

The upper clamp means 31 is affixed to a vertical slide element 39 that is slidable in an upstanding guide mechanism 41 attached to the lower clamp means 29. Therefore, as platen 19 moves upwardly to apply a vertical load to holder 10, the upper clamp means 31 experiences a downward motion relative to clamp means 29. Such relative motion causes the vertical load to be applied to test specimen 12. Eventually the vertical loadings produce a buckling of the test specimen in zone 27. As indicated previously, the magnitude of the load at the moment of specimen buckling is representative of the edgewise compressive strength of the specimen.

In order to insert a specimen into the slot-like space defined by clamp means 29 and 31, it is necessary to first retract each clamp pad 35 or 36 horizontally away from each associated vertical wall 33 or 34. Each pad 35 or 36 is connected to a horizontal rod (or shaft) 43 that extends through a manually operable nut 45 located within a channel 47. Each channel 47 is bolted to the associated clamp means 29 or 31.

Each nut 45 has internal threads in mesh with an externally threaded area of the associated rod 43, whereby manual rotation of each nut in a particular direction draws rod 43 rightwardly, thereby retracting the respective clamp pad 35 or 36 away from the associated vertical wall 33 or 34. By retracting the clamp pads 35 and 36 it is possible to widen the spaces between the pads and the respective vertical walls 33 and 34, thereby permitting a test specimen to be manually moved into the defined slot-like space. The insertional movement of the test specimen is horizontal and normal to the plane of the paper, in FIG. 7.

FIG. 2, is a right end elevational view, of the FIG. 1 specimen holder.

Figure 3:
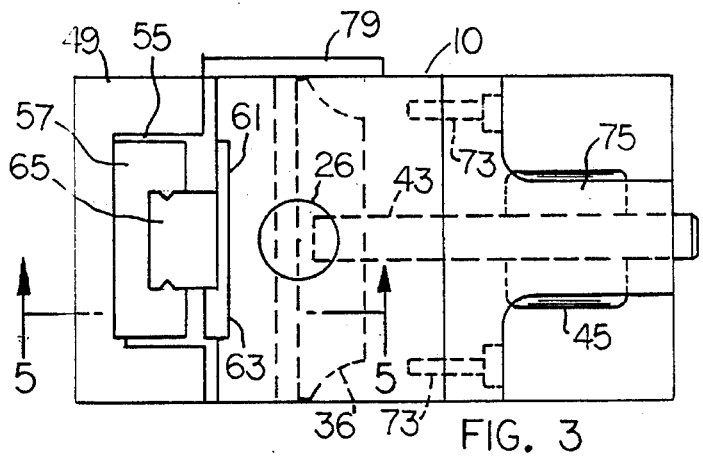
FIG. 3, is a top plan view, of the FIG. 1 holder structure.

FIG. 3, is a top plan view, of the FIG. 1 holder structure.

Figure 4:
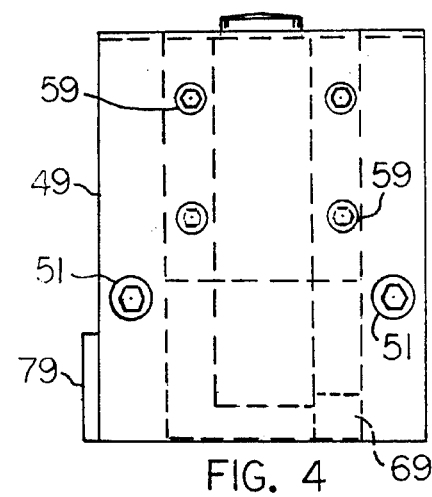
FIG. 4, is a left end elevational view, of the FIG. 1 structure.

FIG. 4, is a left end elevational view, of the FIG. 1 structure.

Figure 5:
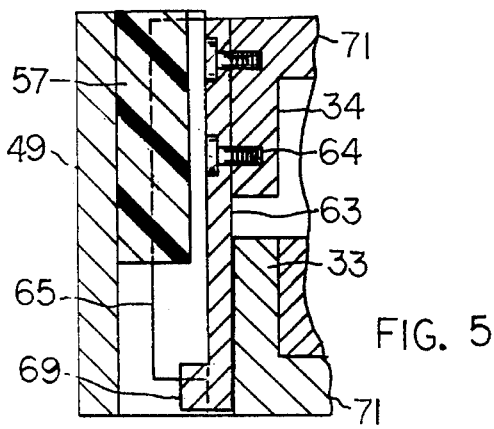
FIG. 5, is a fragmentary sectional view, taken on line 5—5 in FIG. 3.

FIG. 5, is a fragmentary sectional view, taken on line 5—5 in FIG. 3.

FIG. 7, shows the external features of a test specimen holder embodying the invention. FIGS. 1 through 5 show internal features not apparent from FIG. 7. Referring to FIGS. 1, 3 and 4, the aforementioned guide mechanism 41 comprises an upright steel block 49 secured to vertical wall 33 by two machine screws 51 (FIG. 4). Steel block 49 has a vertical recess 55 that accommodates a plastic guide element 57. Four machine screws 59 (FIG. 4) secure the plastic guide element 57 to the upright steel block 49.

The upper clamp means 31 includes a vertical wall 34 that is secured to a two piece slide element 61. Slide element 61 comprises a vertical steel plate 63 secured to wall 34 by machine screws 64, and an elongated steel block 65 secured to plate 63 by machine screws 67 (FIG. 1). Slide element 61 is formed in two pieces primarily for manufacturing reasons.

As shown in FIG. 3, slide block 65 has two vertical grooves that mate with vertical ribs formed on guide element 57. The ribs and grooves interlock to prevent slide element 61 from laterally separating from the fixed guide mechanism 41. At the same time, the slide element 61 is freely movable in the vertical direction. Complete vertical separation of slide element 61 from guide mechanism 41 is prevented by a projection 69 on the lower end of plate 63. As slide element 61 moves upwardly in guide mechanism 41, projection 69 contacts the lower end of plastic guide element 57, to limit the upward stroke of slide element 61. FIG. 1 shows, in dashed lines, the upper clamp means 31 in a partially raised (elevated) position.

Each vertical wall 33 or 34 is integral with a horizontal wall 71 that forms a slide surface for the associated pad 35 or 36. The aforementioned channels 47 are secured to the right ends of horizontal walls 71 by machine screws 73 (FIG. 2). Each channel 47 comprises two vertical flanges and a connecting web 75. As seen in FIG. 3, the web wall 75 has a reduced width compared to the left flange of the channel 47. This is done to facilitate manual access to the associated nuts 45. A person can readily grasp either nut 45 with the thumb and first finger, to manually rotate the nut around the rod 43 axis.

Each rod 43 has its left end press fit into the associated clamp pad 35 or 36. Each rod extends rightwardly from the associated pad through the channel 47, such that the rod 43 can move axially (but not rotationally). Each rod 43 has a raised threaded section 77 in mesh with internal threads on the associated nut 45; the entire inner surface of each nut 45 is threaded.

FIG. 1, shows the lower pad 35 in a closed condition, and the upper pad 36 in a retracted condition. The lower pad 35 can be moved to the retracted condition by rotating the lower nut 45 in the direction that will move the nut leftwardly along the rod.

As the lower nut 45 contacts the left flange of the associated channel 47, the nut is prevented from leftward motion; further rotation of the nut causes the lower rod to move rightwardly, thereby pulling pad 36 away from the associated vertical wall 33. The left flange of channel 47 forms a reaction wall that is engageable with the nut 45 for enabling the nut to move the threaded shaft 43 rightwardly.

Assuming both pads 35 and 36 are retracted a sufficient distance away from the associated vertical walls 33 and 34, a test specimen 12 (FIG. 6) can be inserted into the slot-like space defined by the pads and associated walls 33 and 34. First however, it is necessary to raise the upper clamp means 31 a slight distance, as shown by the dashed lines in FIG. 1; this is done to provide a slot vertical dimension greater than the vertical dimension of the specimen. With clamp means 31 in its raised position, the test specimen 12 can be inserted laterally into holder 10 until a side edge of the specimen contacts a stop element 79 (FIG. 3).

When the specimen 12 is located within holder 10 a stop element (plate) 79 prevents the specimen from passing through the holder. The horizontal length of the insertion slot in holder 10 corresponds to the horizontal width dimension 81 of the specimen, so that upper and lower surface areas of the specimen are fully gripped by the clamp surfaces, i.e., along the entire width dimension 81.

With the specimen loosely positioned in holder 10, the upper clamp means 31 is allowed to gravitationally drop down to the FIG. 7 condition, wherein the specimen has predetermined surface areas thereof aligned with the clamp surfaces. Referring to FIG. 1, each pad, 35 or 36 can be advanced against the side face of the specimen by turning nut 45 in the direction that will enable the nut to move rightwardly along the associated rod 43. As the nut moves rightwardly along the rod the coil spring 37 will bias the pad tightly against the specimen surface; also, the left face of the nut 45 will separate from the left flange of channel 47 so that the nut is out of contact with the channel (as shown e.g., by the position of the lower nut in FIG. 1).

When each pad, 35 or 36, is in its specimen-gripping condition the associated nut 45 is separated from channel 47, so that the clamping force is determined solely by the force of coil spring 37. The thickness of the specimen has essentially no effect on the clamping force.

Coil springs 37 are selected to have the same clamping force, e.g., ten pounds per square inch of pad surface. The aim is to have sufficient clamp force to prevent vertical slippage of the specimen, without undesirable surface indentation of the specimen by the pads or associated walls 33 and 34.

In order to assure a good clamping action the clamp surfaces on pads 35, 36 and walls 33 and 34 are preferably constructed, or designed, to have friction gripper properties on the specimen faces. One way of providing the desired high coefficient of friction is to form a thin rubber coating on each clamp surface. Another method is to adhesively coat the clamp surfaces with finely divided grit or sand particles, so that the surfaces have a "sandpaper" character. A further method of effectively achieving a high coefficient of friction is to knurl the clamp surfaces, e.g., by machining, or etching, tiny criss-crossing grooves in the clamp surfaces. Other suitable means of achieving the desired coefficients of friction, are contemplated.

The purpose in providing clamp surfaces having a high coefficient of friction is to prevent vertical slippage of the specimen without using such high clamping pressures as might deform the specimen surface.

The present invention, described above, relates to a Holder for corrugated paperboard test specimen during edge compression test. Features of the present invention are recited in the appended claims. The drawings contained herein necessarily depict structural features and embodiments of the Holder for corrugated paperboard test specimen during edge compression test, useful in the practice of the present invention.

However, it will be appreciated by those skilled in the arts pertaining thereto, that the present invention can be practiced in various alternate forms and configurations. Further, the previous detailed descriptions of the preferred embodiments of the present invention are presented for purposes of clarity of understanding only, and no unnecessary limitations should be implied therefrom. Finally, all appropriate mechanical and functional equivalents to the above, which may be obvious to those skilled in the arts pertaining thereto, are considered to be encompassed within the claims of the present invention.

What is claimed is:

1. A holder for a corrugated paperboard test specimen that is to be tested for edgewise compression strength; said holder comprising:

a support mechanism that includes a vertical slideway (57);

a lower specimen clamp means (29) carried by said support mechanism; and an upper specimen clamp means (31) slidably mounted on said slideway for vertical movement toward or away from said lower clamp means;

each said clamp means comprising a vertical clamping wall (33 or 34) adapted to engage one major face of a test specimen, a horizontally movable clamping pad (35 or 36) adapted to engage the other major face of the test specimen, spring means (37) continually biasing said pad toward the associated vertical wall, and manual actuation means (at 43, 45) for pulling the respective pad away from the associated vertical wall to permit the insertion of a test specimen into the upper and lower clamp means;

each said manual actuation means comprising a reaction wall spaced from said vertical clamping wall, an elongated threaded element (43) extending from said vertical clamping wall across said reaction wall, and a manually rotatable nut (45) on said threaded element;

each said nut being rotatable in one direction to exert a force on the associated reaction wall, whereby the associated pad is pulled away from the associated vertical clamping wall; and each said nut being rotatable in a reverse direction to allow the associated spring means to bias the pad toward the vertical clamping wall.

2. The holder of claim 1, wherein each said threaded element is an elongated rod extending from the associated clamping pad through the associated reaction wall.

3. The holder of claim 1, wherein each said threaded element is an elongated rod extending from the associated clamping pad through the associated reaction wall; and each said spring means is a coil spring encircling the associated rod between the clamping pad and the reaction wall.

4. The holder of claim 1, wherein said support mechanism comprises a vertical block (49) having a vertical recess therein;

said vertical slideway comprising a guide element (57) located in said recess;

said lower clamp means comprising the aforementioned vertical wall (33) secured to said vertical block and a horizontal wall (71) extending from said vertical wall; and the movable pad of said lower clamp means being slidably mounted on said horizontal wall for movement toward or away from said vertical wall.

5. The holder of claim 4, wherein said upper clamp means comprises a slide element (61) slidably mounted on said guide element for vertical movement, a second vertical clamping wall (34) affixed to said slide element, and a second horizontal wall (71) extending from said second vertical wall; and the clamping pad of said upper clamp means being slidably mounted on said second horizontal wall for movement toward or away from said second vertical wall.

6. The holder of claim 5, wherein each clamping means comprises a channel (47) secured to said horizontal wall of the respective clamping means;

each channel comprising a web (75) located in the plane of the associated horizontal wall, and two flanges extending from said web; and one of said flanges constituting the aforementioned reaction wall of the respective clamping means.

7. The holder of claim 6, wherein each said nut is located within the respective channel; and each said elongated threaded element (43) extending through the channel flanges so that the flanges form bearings for the threaded elements.

8. The holder of claim 5, and further comprising a stop element (69) projecting from said slide element in vertical registry with said block (49), whereby said stop element limits upward vertical movement of said upper clamp means.

\* \* \* \* \*